(12) United States Patent
Hurlimann et al.

(10) Patent No.: US 8,278,922 B2
(45) Date of Patent: Oct. 2, 2012

(54) CONTINUOUS WETTABILITY LOGGING BASED ON NMR MEASUREMENTS

(75) Inventors: Martin D. Hurlimann, Newton, MA (US); Yi-Qiao Song, Newton Center, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 515 days.

(21) Appl. No.: 12/409,102

(22) Filed: Mar. 23, 2009

(65) Prior Publication Data

US 2010/0237860 A1 Sep. 23, 2010

(51) Int. Cl.
*G01V 3/00* (2006.01)

(52) U.S. Cl. ........................ 324/303; 324/306

(58) Field of Classification Search ............ 324/303, 324/306, 318, 322
See application file for complete search history.

(56) References Cited

U.S. PATENT DOCUMENTS

| | | | |
|---|---|---|---|
| 6,229,308 B1 | 5/2001 | Freedman | |
| 6,366,087 B1 | 4/2002 | Coates et al. | |
| 6,570,382 B1 | 5/2003 | Hurlimann et al. | |
| 6,703,832 B2 * | 3/2004 | Heaton et al. | 324/303 |
| 6,765,380 B2 * | 7/2004 | Freedman et al. | 324/303 |
| 6,883,702 B2 | 4/2005 | Hurlimann et al. | |
| 7,034,528 B2 | 4/2006 | Minh et al. | |
| 7,388,374 B2 | 6/2008 | Minh et al. | |
| 7,397,240 B2 * | 7/2008 | Fleury et al. | 324/303 |

OTHER PUBLICATIONS

M. D. Hürlimann et al., "Diffusion-Editing: New NMR Measurement of Saturation and Pore Geometry," SPWLA 43rd Annual Logging Symposium, Jun. 2002: pp. 1-14.
Ridvan Akkurt et al., "Enhanced Diffusion: Expanding the Range of NMR Direct Hydrocarbon-Typing Applications," SPWLA 39th Annual Logging Symposium, May 1998: pp. 1-14.
Gigi Qian Zhang et al., "Interpretation of Wettability in Sandstones with NMR Analysis," Petrophysics, May-Jun. 2000, vol. 41(3): pp. 223-233.
M. G. Prammer et al., "Lithology-Independent Gas Detection by Gradient-NMR Logging," Society of Petroleum Engineers, SPE Annual Technical Conference & Exhibition, Oct. 1995: pp. 325-336.
Robert J. S. Brown et al., "Measurements of Fractional Wettability of Oil Fields' Rocks by the Nuclear Magnetic Relaxation Method," 31st Annual Fall Meeting of the Petroleum Branch of the American Institute of Mining, Metallurgical, and Petroleum Engineers, Oct. 1956, Paper No. 743-G: pp. 1-4.
R. Akkurt et al., "NMR Logging of Natural Gas Reservoirs," SPWLA 36th Annual Logging Symposium, Jun. 1995: pp. 1-12.
Earl Amott, "Observations Relating to the Wettability of Porous Rock," Petroleum Transactions, 1959, vol. 216: pp. 156-162.

(Continued)

*Primary Examiner* — Louis Arana

(57) ABSTRACT

A method for utilizing received formation data to determine one or more fluid instance such as reservoir wettability while in one of a subterranean environment or a surface environment. The method comprising: (a) obtaining at least one set of formation data wherein the set of formation data includes magnetic resonance data from two or more samples within an approximate common characteristic region in the reservoir; (b) computing from the at least one set of received formation data a first fluid instance of the one or more fluid instance using at least two mathematical variables from the group consisting of one of oil saturation, water saturation, $T_1$, $T_2$, diffusion coefficient, tortuosity from long time diffusion coefficient or some combination thereof; and (c) interpreting the computed first fluid instance as at least one wettability property between the fluids in a formation located in the subterranean environment and the formation.

23 Claims, 6 Drawing Sheets

OTHER PUBLICATIONS

W. F. J. Slijkerman et al., "Processing of Multi-Acquisition NMR Data," Society of Petroleum Engineers, 1999 SPE Annual Technical Conference and Exhibition, Oct. 1999: pp. 2-7.

Forrest F. Craig, Jr., "Chapter 2: Basic-Water-Oil Flow Properties of Reservoir Rock," The Reservoir Engineering Aspects of Waterflooding, Dallas: Society of Petroleum Engineers of AIME, 1971: pp. 12-28.

Pabitra N. Sen, "Time-Dependent Diffusion Coefficient as a Probe of Geometry," Concepts in Magnetic Resonance Part A, 2004, vol. 23A(1): pp. 1-21.

Norman R. Morrow, "Wettabiity and Its Effect on Oil Recovery," Society of Petroleum Engineers, JPT, Dec. 1990: pp. 1476-1484.

Erle C. Donaldson et al., "Wettability Determination and Its Effect on Recovery Efficiency," Society of Petroleum Engineers Journal, Mar. 1969: pp. 13-20.

W. Looyestijn et al., "Wettability Index Determination by Nuclear Magnetic Resonance," Society of Petroleum Engineers, 14th SPE Middle East Oil & Gas Show and Conference, Mar. 2005: pp. 1-8.

Michel Robin et al., "Wettability Studies at the Pore Level: A New Approach by Use of Cryo-SEM," SPE Formation Evaluation, Mar. 1995: pp. 11-19.

Freedman et al., "Wettability, Saturation, and Viscosity From NMR Measurements," SPE Journal, Dec. 2003: pp. 317-327.

\* cited by examiner

CONTINUOUS WETTABILITY LOGGING BASED ON NMR MEASUREMENTS

BACKGROUND OF THE INVENTION

1. Field of the Invention

This invention generally relates to methods for determining wettability of fluids in a reservoir using nuclear magnetic resonance data (NMR).

2. Background of the Invention

Wettability is a critical issue in many carbonate reservoirs. Such reservoirs often show significant variability in wettability, even within one formation. The term wettability can be understood as the tendency of a fluid to spread on and preferentially adhere to or "wet" a solid surface in the presence of other immiscible fluids. Knowledge of the wettability of an oil reservoir is important to reservoir and production engineers because reservoir wettability influences reservoir properties such as residual oil saturation, relative permeability, and capillary pressure. See F. G. Craig in the Society of Professional Engineers (SPE) Monograph on "The Reservoir Engineering Aspects of Waterflooding", 1971. Thus, reservoir wettability information is crucial for efficient oil recovery. This information is becoming increasingly important as secondary and tertiary recovery methods are used to recover remaining reserves in old producing fields. For example, in a water-wet reservoir, a waterflood can be an efficient method of recovering remaining reserves after primary production, whereas, in a mixed-wet reservoir, a surfactant flood would be more effective in recovering the remaining oil.

A Standard Laboratory Wettability Measurement

The flow rate of oil through a rock under a pressure gradient is described by the product of permeability, k and relative permeability, $k_r$. Permeability is a geometrical quantity and is determined by the geometry of the pore space. The relative permeability, on the other hand, is controlled by the configuration of the fluid phase within the pore space. Wettability strongly affects this configuration.

For this reason, wettability of a crude oil/brine/rock system is of central importance in determining the efficiency of oil recovery by water displacement in oil reservoirs. According to W. Looyestijn and J. Hofman (W. Looyestijn and J. Hofman. Titled "Wettability-index determination by nuclear magnetic resonance," SPE, Reservoir Evaluation and Engineering, April 2006: p. 146-153) (hereafter "Looyestijn 2006"), in many Middle Eastern carbonate fields, wettability is rated as one of the critical uncertainties.

Measuring wettability is time consuming and notoriously difficult to measure reliably. In the laboratory, wettability is usually characterized by the Amott index (E. Amott, titled "Observations relating to the wettability of porous rock," Trans. AIME, 216: p. 156-162, (1959)), or the USBM index (E. C. Donaldson, R. D. Thomas, and P. B. Lorenz, titled "Wettability determination and its effect on recovery efficiency," SPEJ, March 1969: p. 13-20). The core samples are first brought to the desired saturation and then the downhole wettability is attempted to be restored by aging the sample at an elevated temperature for typically four weeks. The resulting wettability index gives an average value for the core. However, it is well known that the wettability in a reservoir is likely to vary spatially and with production. In addition, Robin et al. (M. Robin, E. Rosenberg, and O. Fassi-Fihri, titled "Wettability studies at the pore level: A new approach by use of Cryo-SEM," SPE Formation Evaluation, March 1995: p. 11-19) measured the fluid configuration in rocks at the micron level using cryo-SEM and reported heterogeneity of wettability at the pore level.

However, this implies that an average wettability index can be misleading to predict the fluid configuration inside the core. Clearly, a direct measurement of the fluid configuration downhole will circumvent many of the present difficulties.

At least one widely-used wettability indicator is the use of contact angles in water-oil-solid systems. In addition, other laboratory tests for wettability are also available, including imbibition measurements. However, these are laboratory measurements and cannot be performed downhole. In contrast, a nuclear magnetic resonance (NMR) approach can provide a qualitative wettability indicator and has the advantage of being able to assess the fluids and rock at reservoir conditions.

NMR measurements on fluid saturated rocks are sensitive to the wettability of the rock matrix because relaxation rates of fluid molecules are enhanced when they are in contact with rock surfaces. This is because rock surfaces often have paramagnetic ions or magnetic ions which can provide efficient relaxation for the fluid molecules. Reservoir wettability not only depends on the inherent property of the rock matrix, but also on surface interactions between the rock matrix and the fluid molecules, i.e., it also depends on the attractive forces that exist between the polar oil molecules and those on rock matrix surfaces.

Many laboratory NMR wettability studies have been reported in the literature. The first NMR study on wettability was by Brown and Fatt, who made $T_1$ relaxation measurements on water-saturated unconsolidated sand packs constructed with different fractions of water-wet and oil-wet sand grains. See R. J. S. Brown and I. Fatt, "Measurements of Fractional Wettability of Oilfield Rocks by the Nuclear Magnetic Relaxation Method," Petroleum Transactions, AIME, 207, pp. 262-264, 1956. Numerous studies on the application of NMR to wettability have been published since then. See Q. Zhang, C. C. Huang, and G. J. Hirasaki, "Interpretation of Wettability in Sandstones with NMR Analysis," Petrophysics, May-June, 2000, vol. 41, No. 3, pp. 223-233.

Prior NMR studies of wettability of partially saturated reservoir rocks have been mostly limited to rocks saturated with brine and low viscosity hydrocarbons, such as Soltrol, decane, and dodecane. These low viscosity fluids are characterized as having narrow $T_1$ and $T_2$ distributions and long relaxation times. Accordingly, it is relatively simple to distinguish the hydrocarbon signal from the brine signal in the relaxation time distributions of partially saturated rocks. The oil relaxation times in the rocks can then be compared with those of the bulk hydrocarbon (i.e., outside the rock) to infer whether the oil is wetting the surface. However, wettability inferred from experiments using refined or pure hydrocarbons is not indicative of the wettability of the same rocks saturated with crude oil, because crude oils may contain asphaltenes and resins, which are known to have surface-active polar molecules that are attracted to opposite charge sites on the pore surfaces.

The above described approaches to the determination of rock wettability use laboratory measurements. Reservoir wettability determination from laboratory measurements is not definitive because it is not possible to accurately mimic reservoir conditions in the laboratory, as noted above. In fact, the very processes required to obtain laboratory samples can alter the reservoir wettability. See N. R. Morrow, "Wettability and Its Effect on Oil Recovery" in the J. of Pet. Tech., December, 1990, pp. 1476 1484.

As discussed above, both water and hydrocarbons in earth formations produce detectable NMR signals. Thus, it is desirable for at least one method for determining wettability that the signals from water and hydrocarbons be separable so that hydrocarbon-bearing zones may be identified. However, it is not always easy to distinguish which signals are from water and which are from hydrocarbons. Various methods have been proposed to separately identify water and hydrocarbon signals.

Known Methods for Separately Identifying Water and Hydrocarbon Signals

The differential spectrum (DSM) and shifted spectrum (SSM) methods proposed by Akkurt et al. in "NMR Logging of Natural Gas Reservoirs" Paper N. Transactions of the Society of Professional Well Log Analysts (SPWLA) Annual Logging Symposium, 1995, compare $T_2$ distributions derived from two Carr-Purcell-Meiboom-Gill (CPMG) measurements performed with different polarization times (DSM) or echo-spacings (SSM). A modification to these methods, known as time domain analysis (TDA), was later introduced by Prammer et al. in "Lithology-Independent Gas Detection by Gradient-NMR Logging," SPE paper 30562, 1995. In TDA, "difference" data are computed directly in the time domain by subtracting one set of the measured amplitudes from the other. The difference dataset is then assumed to contain only light oil and/or gas. In TDA, relative contributions from light oil or gas are derived by performing a linear least squares analysis of the difference data using assumed NMR responses for these fluids. Both DSM and TDA assume that the water signal has substantially shorter $T_1$ relaxation times than those of the hydrocarbons. This assumption is not always valid, however. Most notably, this assumption fails in formations where there are large pores or where the hydrocarbon is of intermediate or high viscosity. The SSM method and its successor, the enhanced diffusion method (EDM) proposed by Akkurt et al. in "Enhanced Diffusion: Expanding the Range of NMR Direct Hydrocarbon Typing Applications", Paper GG. Transactions of the Society of Professional Well Log Analysts (SPWLA) Annual Logging Symposium, 1998, separate gas, oil and water contributions based on changes in the $T_2$ distributions that result from changes in the echo spacing of CPMG measurements. The methods are applicable in a limited range of circumstances and the accuracy of the result is significantly compromised by incomplete separation of water and hydrocarbon signals in the $T_2$ domain. Moreover, these methods are designed to function with CPMG sequences. However, with the diffusion-based methods, CPMG pulse sequences provide poor signal to noise ratios due to the reduced number of echoes that can be measured. A strategy for combining and selecting these different NMR methods has been described recently by Coates et al. in U.S. Pat. No. 6,366,087.

The diffusion-editing (DE) pulse sequence by Hurlimann et al. provides a different approach. See M. D. Hurlimann et al., "Diffusion-Editing: New NMR Measurement of Saturation and Pore Geometry," paper presented at the 2002 Annual Meeting of the Society of Professional Well Log Analysts, Osio, Japan, Jun. 2 5; see also, U.S. Pat. No. 6,570,382, filed on Nov. 28, 2000, by Hurlimann. This patent is assigned to the same assignee as the present invention and is hereby incorporated by reference. DE pulse sequences are similar to the CPMG sequences except that the initial two echoes are acquired with longer echo spacings and the third and subsequent echoes are acquired with shorter echo spacings. In DE pulse sequences, diffusion information is encoded during the acquisition of the first two echoes, whereas the third and subsequent echoes provide bulk and surface relaxation time information with relatively little attenuation of the signal by diffusion. Using a conventional CPMG sequence to encode the diffusion information requires a long inter-echo spacing, which results in poor bulk and surface relaxation time information because diffusion decay attenuates the signal after relatively few echoes. Consequently, a suite of data acquired with DE sequences provides better diffusion information and signal-to-noise ratio in the spin-echo data, as compared to an analogous suite acquired with CPMG sequences. Therefore, DE sequences can provide more accurate and robust computations of brine and oil $T_2$ distributions than CPMG sequences.

In addition to DE sequences, specialized interpretation methods have been developed for NMR data in order to further enhance hydrocarbon detection. These methods typically apply forward modeling to suites of NMR data acquired with different parameters. The suite of NMR data are typically acquired with different echo spacings (TE) or polarization times (WT), and sometimes acquired with different magnetic field gradients (G). DE sequences are one example of such data acquisition. Two exemplary methods include: the MACNMR proposed by Slijkerman et al., SPE paper 56768, "Processing of Multi-Acquisition NMR Data", 1999, and the Magnetic Resonance Fluid characterization (MRF) method disclosed in U.S. Pat. No. 6,229,308 B1 issued to Freedman and assigned to the assignee of the present invention ("the Freedman patent"). The Freedman patent is hereby incorporated by reference.

The Magnetic Resonance Fluid characterization (MRF) method is capable of obtaining separate oil and water $T_2$ distributions. This method uses a Constituent Viscosity Model (CVM), which relates relaxation time and diffusion rates to constituent viscosities whose geometric mean is identical to the macroscopic fluid viscosity. With the MRF method, estimates for water and hydrocarbon volumes are obtained by applying a forward model to simulate the NMR responses to a suite of NMR measurements acquired with different parameters. Specifically, The MRF technique is based on established physical laws which are calibrated empirically to account for the downhole fluid NMR responses. By using realistic fluid models, MRF aims to minimize the number of adjustable parameters to be compatible with the information content of typical NMR log data. Since the model parameters are by design related to the individual fluid volumes and properties, determination of the parameter values (i.e. data-fitting) leads directly to estimates for petrophysical quantities of interest.

The forward-model approach relies on the validity of the fluid models employed. In "non-ideal" situations where fluid NMR responses deviate from the model behavior (oil-wet rocks, restricted diffusion), these techniques may lead to erroneous answers. In some circumstances, "non-ideal" responses may be identified by poor fit-quality, in which case the fluid models can be adjusted by modifying the appropriate model parameter. However, it may not be obvious which element of the fluid model should be modified and what modification is needed.

While the above mentioned prior art methods are useful in predicting the presence of hydrocarbons in the formations, it is desirable to have new methods that can utilized the gathered data such as electrical conductivity data, NMR data and/or in combination with other saturation and porosity measurements (e.g., resistivity, neutron and gamma rays), so as to determine fluid configurations and wettability properties in the formations.

Therefore, there is a need for methods that can determine reservoir wettability either under downhole conditions or on the surface, by non-limiting example, so as to provide for efficient oil recovery.

SUMMARY OF THE INVENTION

According to at least one embodiment of the invention, the invention can include a method for utilizing received formation data to determine one or more fluid instance such as reservoir wettability while in one of a subterranean environment or a surface environment. The method comprising: (a) obtaining at least one set of formation data wherein the at least one set of formation data includes magnetic resonance data from two or more samples within an approximate common characteristic region in the reservoir; (b) computing from the at least one set of received formation data a first fluid instance of the one or more fluid instance using at least two mathematical variables from the group consisting of one of oil saturation, water saturation, $T_1$, $T_2$, diffusion coefficient, tortuosity from long time diffusion coefficient or some combination thereof; and (c) interpreting the computed first fluid instance as at least one wettability property between the fluids in a formation located in the subterranean environment and the formation.

According to an aspect of the invention, the invention can include the approximate common characteristic region in the reservoir having one of reservoir wettability, mineralogy and at least two fluids, some combination thereof. Further, the interpreting of the computed first fluid instance can further include displaying the results for the computed first fluid instance as an at least two-axis graph and identifying the first fluid instance on the graph representing a wettability property between the fluids in the formation and the formation. Further still, the one or more fluid instance can be from the group consisting of relative permeability, residual oil saturation, formation factors, Archie's exponents, or any combination thereof. It is also possible, the received formation data can be Nuclear Magnetic Resonance (NMR) data. Further, the NMR data can include one of $T_1$, $T_2$, diffusion coefficient, multi-dimensional NMR data, tortuosity from long time diffusion coefficient or some combination thereof. Further still, the received formation data can be diffusion data at different saturations so as to extract a plurality of Archie exponents. It is possible, the reservoir wettability can be displayed along a saturation axis and one of a $1/T_2$ axis, $T_{2,LM}$ axis, $T_2$, average $T_2$, average$1/T_2$. Moreover, the invention may include the reservoir wettability that could be displayed along a saturation axis and one of a $1/T_1$ axis, $T_{1,LM}$ axis, $T_1$, average $T_1$, average$1/T_1$.

According to an aspect of the invention, the invention can include the reservoir wettability displayed that includes one of a oil wettability graph, a water wettability graph or both the oil wettability graph and the water wettability graph. Further, obtaining the at least one set of formation data can be performed with one of a wireline tool or a measurement-while-drilling tool. Further still, obtaining the at least one set of formation data can be performed with a nuclear magnetic resonance module in a sidewall coring tool at a selected axial depth. It is possible the method can include obtaining the at least one set of formation data is performed with a nuclear magnetic resonance instrument after removing at least one sample from the reservoir such that the at least one sample is transferred to the surface environment.

According to at least another embodiment of the invention, the invention can include a method for utilizing received Nuclear Magnetic Resonance (NMR) data to determine one or more fluid instance while in one of a reservoir or a surface environment for an oilfield application. The method comprising: (a) obtaining NMR data from two or more samples within an approximate common characteristic region in the reservoir; (b) computing from the received NMR data a first fluid instance of the one or more fluid instance using at least two mathematical variables from the group consisting of one of oil saturation, water saturation, $T_1$, $T_2$, diffusion coefficient, tortuosity from long time diffusion coefficient or some combination thereof; and (c) interpreting the computed first fluid instance as at least one wettability property between the fluids in a formation located in the reservoir and the formation.

According to an aspect of the invention, the invention can include the approximate common characteristic region in the reservoir having one of reservoir wettability, mineralogy and at least two fluids, some combination thereof. Further, the one or more fluid instance is from the group consisting of relative permeability, residue oil saturation, formation factors, Archie's exponents, or any combination thereof. Further still, another fluid instance of one or more fluid instance is from the group consisting of relative permeability, residual oil saturation, formation factors, Archie's exponents, or any combination thereof. It is possible the invention can include computing from the received NMR data of the another fluid instance from the group of the one or more fluid instance using at least two mathematical variables from the group consisting of one of oil saturation, water saturation, $T_1$, $T_2$, diffusion coefficient, tortuosity from long time diffusion coefficient or some combination thereof, further includes displaying the results for the computed another fluid instance as an at least two-axis graph, and then identifying from the another fluid instance on the at least two-axis graph at least one other wettability property between the fluids in the formation and the formation. Further, the received NMR data can be diffusion data at different saturations so as to extract a plurality of Archie exponents. Further still, the interpreting of the computed first fluid instance further includes displaying the results for the computed first fluid instance as an at least two-axis graph and identifying the first fluid instance on the graph representing a wettability property between the fluids in the formation and the formation.

According to another aspect of the invention, the invention can include the wettability displayed includes one of a oil wettability graph, a water wettability graph or both the oil wettability graph and the water wettability graph. Further, obtaining the at least one set of NMR data can be performed with one of a wireline tool or a measurement-while-drilling tool. Further still, obtaining the at least one set of NMR data can be performed with a nuclear magnetic resonance instrument after removing the two or more samples from a earth formation such that the two or more samples are transferred to the surface environment.

According to at least another embodiment of the invention, the invention can include a method of formation evaluation from nuclear magnetic resonance (NMR) data, the method comprising: (a) obtaining a set of NMR data from samples having at least two saturations in a reservoir within an approximate common characteristic region in the reservoir; (b) computing from the set of NMR data at each saturation of the at least two saturations, properties of each fluid of the samples; and (c) comparing the determined properties of samples to determine one of wettability, fluid configurations or other fluid characteristics.

According to an aspect of the invention, the invention can include the other fluid characteristics include one of residual oil saturation, relative permeability, formation factors, Archie's exponents, or any combination thereof. Further, the approximate common characteristic region in the reservoir includes one of reservoir wettability, mineralogy and at least two fluids, some combination thereof.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PREFERRED EMBODIMENTS

Figure 1A:
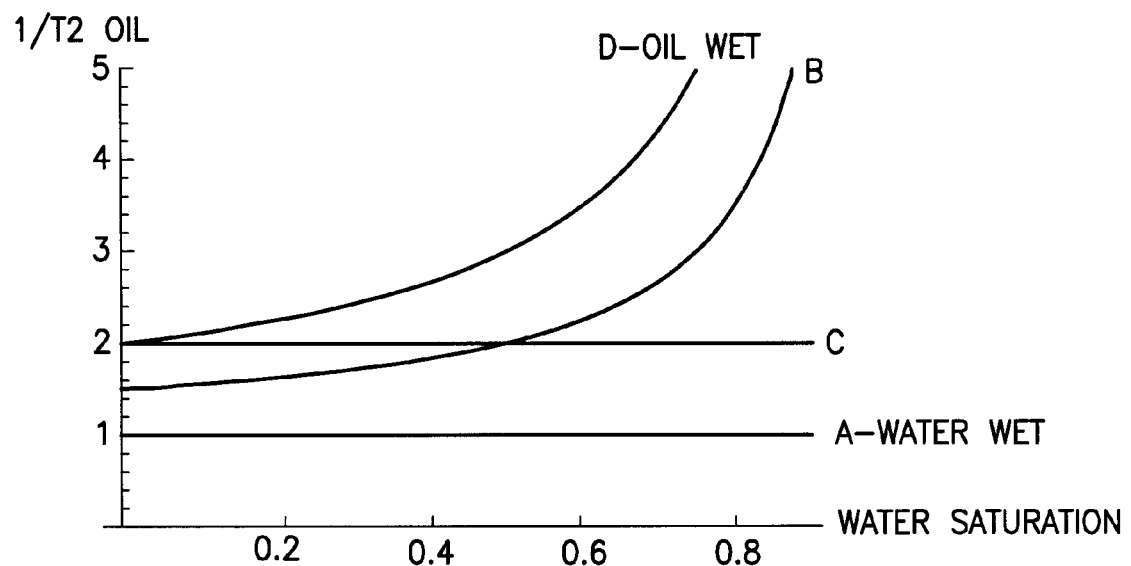
FIG. 1 illustrates the saturation dependence of $T_2$ for several fluid configurations (A, B, C and D), such that the plots assume the following constants: $\rho_o=1$ μm/s, $\rho w=5$ μm/s, bulk $T_2$ is 1 s for oil and water, and for case B, the wettability is neutral and oil and water assume equal surface in accordance with embodiments of the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

According to at least one embodiment of the invention, the invention can include a method for utilizing received formation data to determine one or more fluid instance such as reservoir wettability while in one of a subterranean environment or a surface environment. The method comprising: (a) obtaining at least one set of formation data wherein the at least one set of formation data includes magnetic resonance data from two or more samples within an approximate common characteristic region in the reservoir; (b) computing from the at least one set of received formation data a first fluid instance of the one or more fluid instance using at least two mathematical variables from the group consisting of one of oil saturation, water saturation, $T_1$, $T_2$, diffusion coefficient, tortuosity from long time diffusion coefficient or some combination thereof; and (c) interpreting the computed first fluid instance as at least one wettability property between the fluids in a formation located in the subterranean environment and the formation.

Overview

According to embodiments of the invention, the invention includes a series of NMR approaches to determine wettability. Wettability is particularly important for carbonate reservoirs that can exhibit significant variability, even within one formation. Currently it is believed there is not a commercial service for in situ measurement of wettability. In particular, the invention utilizes features of at least one device, such as an MRScanner that provides for the capability of gathering data relating to detailed fluid analysis and multiple-DOI measurements. Further, this allows for the measurement of $T_1$, $T_2$ and diffusion constant for each fluid phase. The NMR based approaches probes the fluid configuration and can provide an in situ wettability index. This technique can be readily implemented on current devices such as the MRScanner without significant hardware change.

As discussed above, NMR wettability measurements provide for a key advantage from the latest NMR technology which is the ability to detect and separate simultaneously signals from both fluid phases inside the formation. In contrast, resistivity is only sensitive to the conducting (water) phase.

By comparing NMR results from both phases, it is possible to distinguish effects due to pore geometry (which affects both phases) from wettability effects (this is specific for each phase).

Furthermore, with the MRScanner, different depths of investigations (DOI) can be probed. In general, the saturation near the borehole varies with DOI. This allows downhole measurements at different saturations. The invention provides for at least two methods to determine fluid configurations and wettability properties. The first method is based on surface relaxation and incorporates data, e.g., relating to detailed fluid analysis and multiple-DOI measurements. The second method of the at least two methods is based on restricted diffusion.

Relaxation Measurements

It is known that NMR relaxation measurements are sensitive to the fluid arrangements in rocks and that these measurements can be used as a wettability indicator (R. J. S. Brown and I. Fatt, titled "Measurements of fractional wettability of oilfield rocks by the nuclear magnetic relaxation method," Trans. AIME, 207: p. 262, (1956)). The sensitivity stems from surface relaxation. The NMR relaxation rate for a fluid phase f (f=crude oil, water, gas, OBM, . . . ) is in general dominated by two terms due to surface and bulk relaxation:

$$\frac{1}{T_{2,f}} = \frac{1}{T_{2,bf}} + \rho_{gf}\frac{\Sigma_{gf}}{V_f} \qquad \text{Eq. 1}$$

Here $T_{2,bf}$ is the bulk relaxation time and a property of the fluid f. The second term describes surface relaxation that depends on the fluid arrangements. $\Sigma_{gf}$ is the surface area between the fluid of interest and the grains of the rocks. $V_f$ is the volume of the fluid phase f. The surface relaxivity $\rho_{gf}$ describes the efficiency of relaxation of the fluid molecule by the grain surfaces. It is somewhat variable between different rocks and is fluid specific. Rock surfaces often relax water more efficiently than oil. In completely water-wet systems, the oil phase will not make contact with the grain surfaces, and it will relax with the bulk relaxation rate. If the measured relaxation time of oil is faster than the bulk relaxation time, the fluid must be in direct contact with the grain surfaces and the system must be at least partially oil-wet.

We have been issued a number of patents (U.S. Pat. No. 6,765,380 issued to Robert Freedman and M. D. Hurlimann, titled "Determining wettability of an oil reservoir using borehole NMR, measurements"; and U.S. Pat. No. 6,883,702 issued to M. D. Hurlimann, L. Venkataramanan, and C. Straley, titled "Wettability from diffusion editing") that take advantage of diffusion editing to separate the water and oil signal and then assess the importance of surface relaxation to infer wettability. With a tool like the MRScanner, measurements can be performed at different depth of investigations (DOI). This is especially useful if there is a significant variation in saturation at the different DOI. In that case, we can compare surface relaxation of oil and water. At a comparable saturation, the wetting phase will have a larger grain-fluid surface area than the non-wetting phase.

Looyenstijn 2006, as noted above, recently demonstrated in laboratory experiments that it is possible to fit relaxation data of different saturations quantitatively with the simple model and extract an NMR wettability index that correlates well with the USBM wettability index. However, this approach requires the determination or a priori knowledge of a number of parameters, such as the surface relaxivities $\rho_{grain-water}$ and $\rho_{grain-oil}$.

Also, their method obtains wettability index from the total signal of oil and water and it may suffer from the overlap of oil and water $T_2$ spectra.

The essential physics is based on surface relaxation. The NMR $T_2$ relaxation rate of the formation fluid is reduced by an amount proportional to the ratio of the contact surface area and the fluid volume. As a result, the relaxation behavior is a sensitive function of the fluid configuration in pores. There are two general scenarios to consider: one is pore replacement—there is single fluid in an individual pore. The other scenario is partial pore volume replacement and mixtures exist at the pore level. In fact, in rocks with multiple pore sizes, the capillary force may make oil preferably occupies larger pores so that the saturation (and perhaps wettability) may be a function of pore size.

In the case of mixed phase in a single pore, the $T_2$ of either component can be written as:

$$\frac{1}{T_{2w}} = \rho_{2w}\frac{\Sigma_w}{V_w} + \frac{1}{T_{2,bw}} \quad \text{Eq. 2}$$

$$\frac{1}{T_{2o}} = \rho_{2w}\frac{\Sigma_o}{V_o} + \frac{1}{T_{2,bo}} \quad \text{Eq. 3}$$

where $\Sigma_o + \Sigma_2 = \Sigma$ is the total fluid—grain contact surface area, and $V_o + V_w = V$ the total fluid volume. Further, it is noted in Eq.'s 2-3, that "2w" is subscript to "$\rho$", e.g., $\rho_{2w}$. The dependence of $T_2$ as a function of saturation will exhibit different behavior depending on the detailed fluid configurations, as noted below in Case A, B, C and D:

Fully water wet:
Case A: Oil does not touch the surface, completely non-wetting, i.e. water-wet formation. Then $\Sigma_o = 0$ and $$\frac{1}{T_{2o}}$$

will remain at the bulk value and does not change as a function of saturation. For water, $\Sigma_w = \Sigma$, thus $$\frac{1}{T_{2w}}$$

decreases as saturation increases;
Case B: Oil always occupies a fixed fraction of the total surface, $\Sigma_o$=const., and $\Sigma_w$=const. Thus, as water saturation increase, $$\frac{1}{T_{2o}}$$

increases and $$\frac{1}{T_{2w}}$$

decreases;
Case C: Oil surface contact is proportional to oil saturation. Thus, $$\frac{1}{T_{2o}}$$

will remain constant but at a value elevated from the bulk value; and
Case D: Oil always wets the total surface, this is fully oil-wet. Then, $$\frac{1}{T_{2w}}$$

is constant at the bulk value.

$$\frac{1}{T_{2o}}$$

will decrease as oil saturation increases.

Figure 1B:
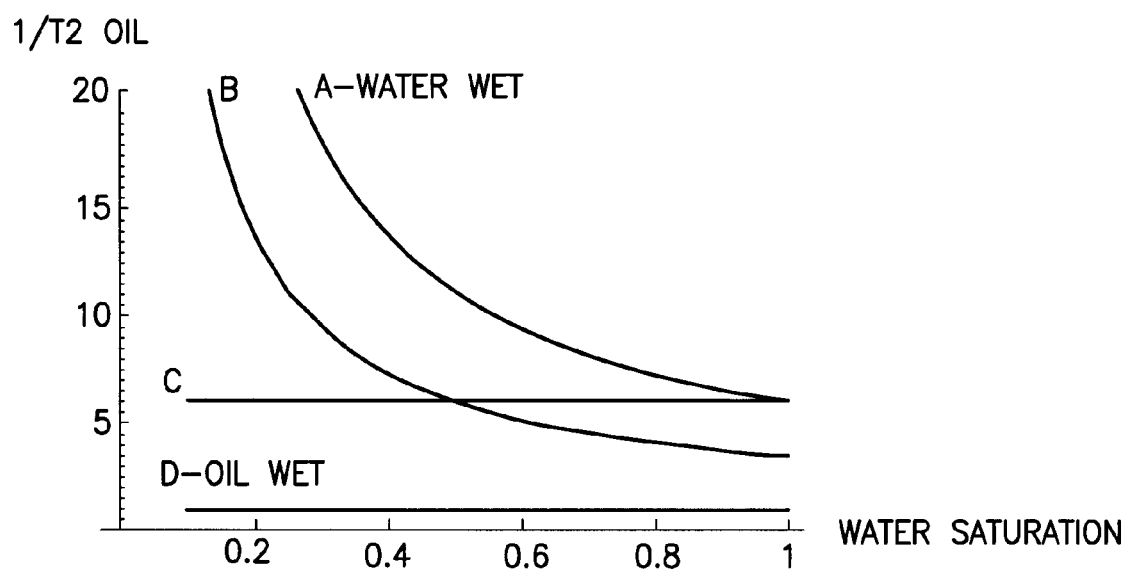

The cases B and C represent partial wetting by oil and water. The four cases are illustrated in FIG. 1. Any combination of these four scenarios, such that they represent different fluid configurations determined by the fluid rock interactions.

Two features of the MRScanner are specifically important for the wettability determination: one is the ability to separate oil and water signals, the second is the ability to obtain signals at different depths (DOI), and thus different saturations (e.g. due to invasion). As a result, reliable in situ measurement of oil and water $T_2$ for different saturations can be obtained in order to plot on a figure similar to FIG. 1. From such plot, one may first determine the essential fluid configuration in the formation and then the wettability index.

Determination of Wettability Through Restricted Diffusion

We disclose here an additional NMR technique to assess wettability. This new method is based on restricted diffusion (P. N. Sen. Time-dependent diffusion coefficient as a probe of geometry. Concepts in Magnetic Resonance, 23A: 1, (2004)). Diffusion of fluid molecules is affected by the configuration of the fluid phase. For short enough diffusion times $t_d$, the mean squared displacement of spins is proportional to $t_d$ and the molecular diffusion coefficient of the fluid, $\langle(x(t_d)-x(0))^2\rangle = 2Dt_d$. If the fluid phase is confined by a dimension that approaches the diffusion length $ld=\sqrt{2Dt_d}$, then the mean squared displacement is smaller than predicted from the molecular diffusion coefficient. We take advantage here of the fact that at long enough diffusion times, there is a simple relationship between restricted diffusion and tortuosity.

Tortuosity of water phase in rock can be measured by the resistivity index. For partially saturated rocks, the tortuosity of the fluid phase has two contributions: the tortuosity of the pore space and the fluid arrangement within this pore space. This is reflected in Archie's ansatz:

$$\frac{\sigma_w}{\sigma_{w,o}} = \phi^m S_w^n \qquad \text{Eq. 4}$$

For most rocks, the tortuosity of the pore space is mainly a function of porosity with m≈2. However, the configuration of the water within the pore space depends on wettability.

$$n \approx 2 \text{ for wetting phase} \qquad \text{Eq. 5}$$

$$n \geq 2 \text{ for non-wetting phase} \qquad \text{Eq. 6}$$

For fully brine saturated cores, is well known that there is a direct relationship between the electrical formation factor and the long time limit of the diffusion coefficient:

$$\frac{D_w}{D_{w,o}} = \frac{1}{\phi} \frac{\sigma_w}{\sigma_{w,o}} = \phi^{m-1} \qquad \text{Eq. 7}$$

The key insight is that it is possible to extend this relationship to partial saturation. In the long time limit, diffusion of the water phase is directly related to the resistivity index as:

$$\frac{D_w}{D_{w,o}} = \frac{1}{\phi S_w} \frac{\sigma_w}{\sigma_{w,o}} \qquad \text{Eq. 8}$$

$$\frac{D_w}{D_{w,o}} = \phi^{m-1} S_w^{n-1} \qquad \text{Eq. 9}$$

In addition, the relationship can be extended to the oil phase. In a thought experiment, let's set the conductivity of the water phase to zero, $\sigma_{w,o}=0$ and that of oil to $\sigma_{o,0}$. In that case, the resistivity index will be probing the oil phase, rather than the water phase, and we can write:

$$\frac{\sigma_o}{\sigma_{o,0}} = \phi^m S_o^{n_o} \qquad \text{Eq. 10}$$

The exponent m will be identical to that in Eq. 4 since it only depends on pore geometry. However, the saturation exponent is sensitive to the fluid configuration within the pore space and will be in general different for the two phases. We use subscripts $n_w$ and $n_o$ to indicate the difference.

With resistivity measurements, it is of course not possible to detect the tortuosity of the oil phase and Eq. 10 appears to be frivolous. However, NMR diffusion measurements allow the measurement of oil tortuosity. In this case, we can write:

$$\frac{D_o}{D_{o,0}} = \phi^{m-1} S_o^{n_o-1} \qquad \text{Eq. 11}$$

$$\frac{D_0}{D_{o,0}} = \phi^{m-1} (1-S_w)^{n_o-1} \qquad \text{Eq. 12}$$

Figure 2:
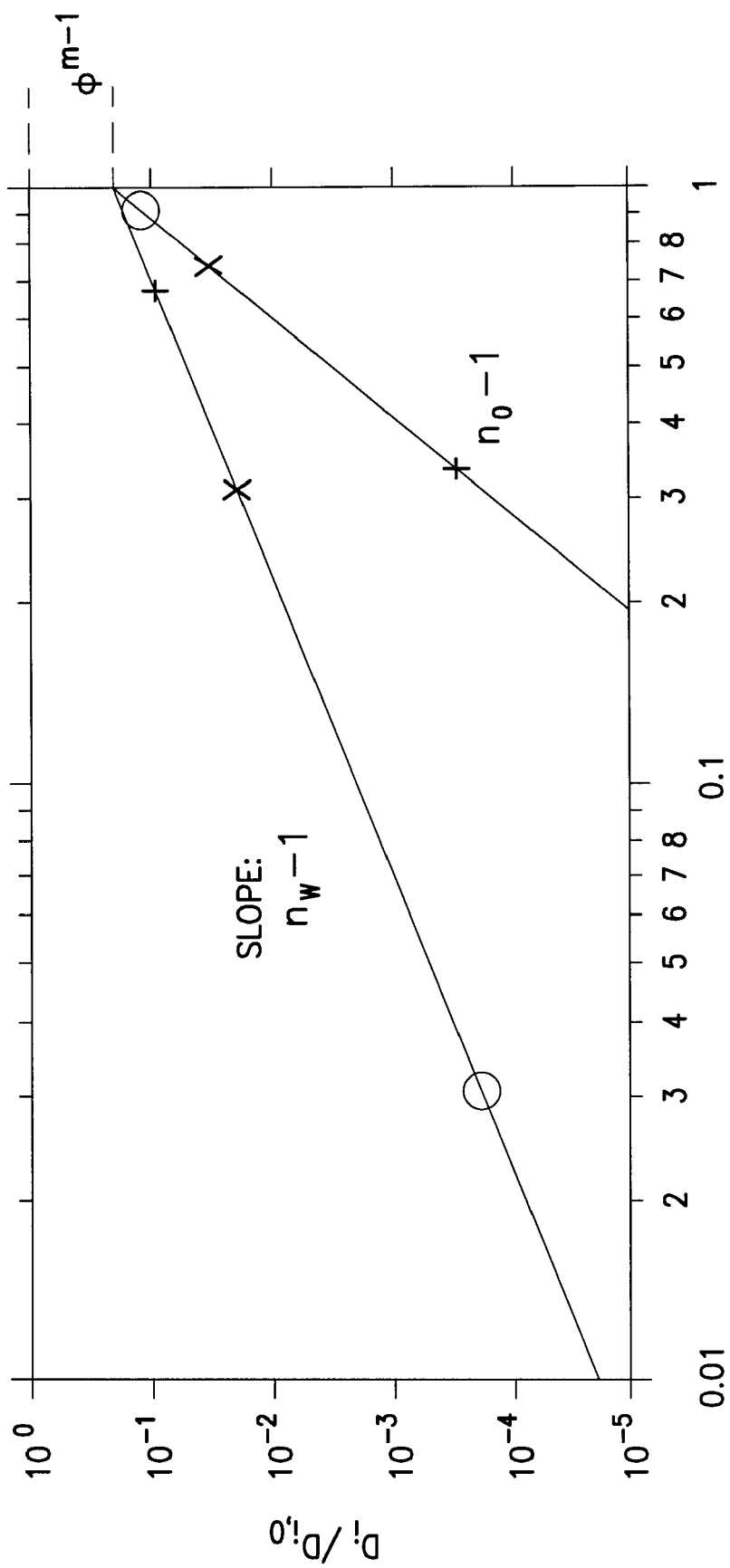
FIG. 2 illustrates the schematic dependence of the normalized diffusion coefficient of phase i, $D_i/D_2$,o versus saturation of phase i, $S_i$ in accordance with embodiments of the invention.

Referring to FIG. 2, FIG. 2 illustrates the results of diffusion vs saturation, assuming that diffusion data at three samples with three different saturations, possibly obtained at three different DOI. The three points could correspond to different DOI. It is noted that it could even be the same zone or even the same depth.

The results for the water and oil phase lie on a straight line if Archie's ansatz is a good description of the saturation dependence. The lines will intersect at 100% saturation at $\phi^{m-1}$. The intersect therefore allows the determination of m. The slopes of the two curves depend on the fluid configuration with the pore space and are given by $n_w^{-1}$ and $n_o^{-1}$, respectively. In general, the wetting phase is better connected than the non-wetting phase at comparable saturation. The wetting phase can form thin films, whereas the non-wetting phase tends to snap off. This difference in connectivity allows the identification of the dominant wetting phase. In addition, the wettability can be inferred from the contrast of the two exponents. For neutral wettability, we expect $n_w \tilde{=} n_o$, whereas $n_w \ll n_o$ for strongly water-wet and $n_o \ll n_w$ for strongly oil-wet cases, respectively.

Note that the determination of the saturation exponents does not depend on the accurate knowledge of the molecular diffusion coefficient of the oil, $D_o$. In fact, the requirement that the two lines intersect at 100% saturation allows the determination of the relative diffusion coefficients $D_o/D_w$. In most cases, the relevant diffusion coefficient for water is known, since it is only strongly affected by temperature.

Even if Archie's ansatz is only a modest approximation, i.e. if the saturation exponents depend on the saturation, the general approach still holds: The tortuosity of the wetting phase is expected to be smaller than the tortuosity of the non-wetting phase.

The analysis above has relied on the assumption that we can measure the long-time limit of restrictions. This can be tested by comparing measurements with different diffusion times and by comparing the measured reduction of the water diffusion coefficient with the resistivity index, through Eq. 4. If the reduction in diffusion coefficient is less than predicted by the electrical measurements, then this is a direct indication that the saturation is not uniform on the length scale $\sqrt{Dt}$.

The following flowcharts show by non-limiting example at least one embodiment of the invention. It is noted that the described flowcharts may be varied in view of the aspects of the whole invention as disclosed herein, and not limited to the specific method disclosed in one or all of the FIG.s.

Figure 3:
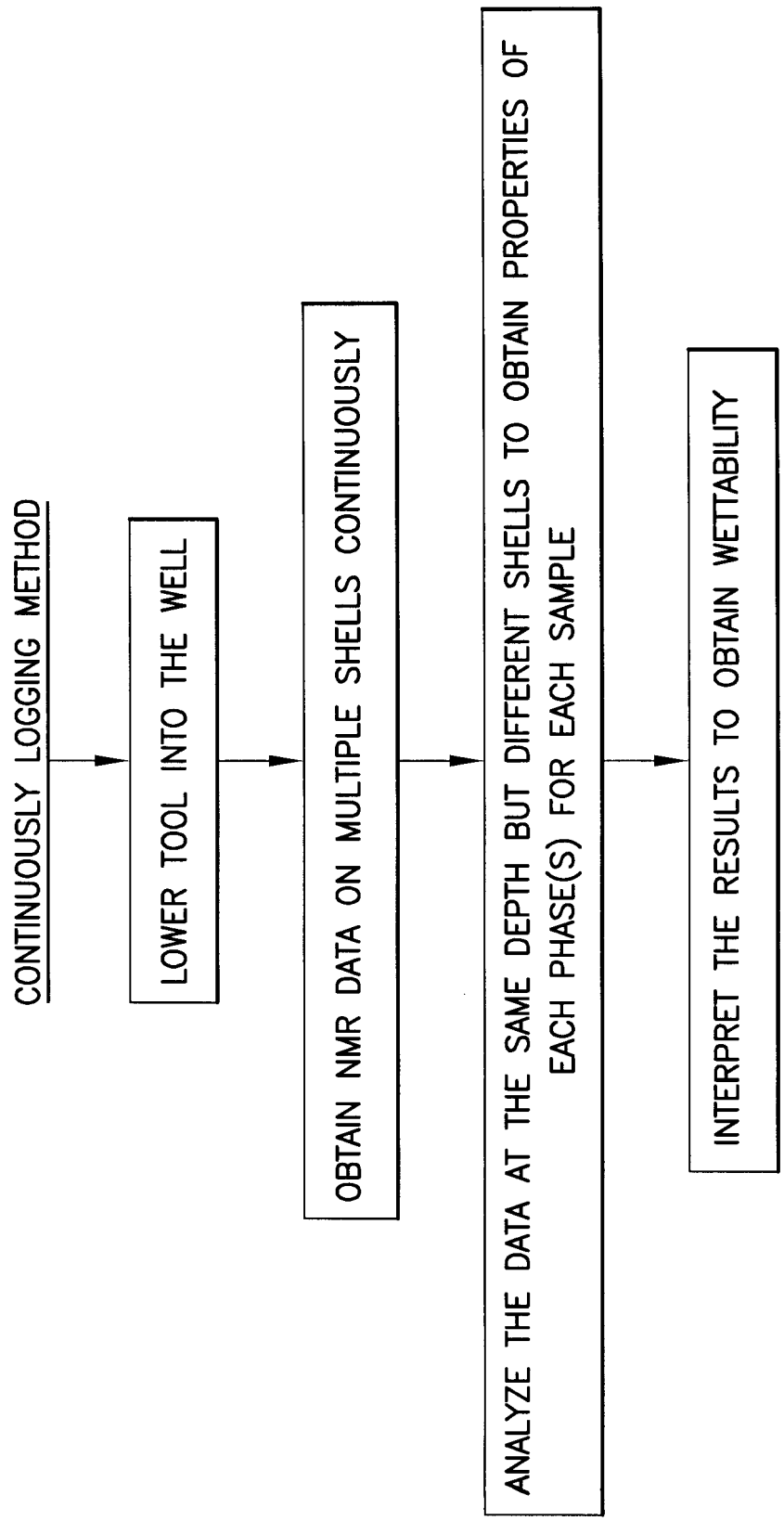
FIG. 3 illustrates at least one continuously logging method according to embodiments of the invention.

FIG. 3 shows a flowchart of at least one continuous logging method according to embodiments of the invention. First lower an NMR logging tool into the well. The tool will operate to execute the appropriate NMR pulse sequences to measure NMR response of the pore fluids at multiple depths of investigation (DOI) and acquires the data continuously as the tool moves through the rock formation. The data for different DOI at the same well location (depth) is then analyzed to extract the wettability property of that location. The logging data is analyzed to obtain wettability properties for the entire interval of the formation.

Figure 4:
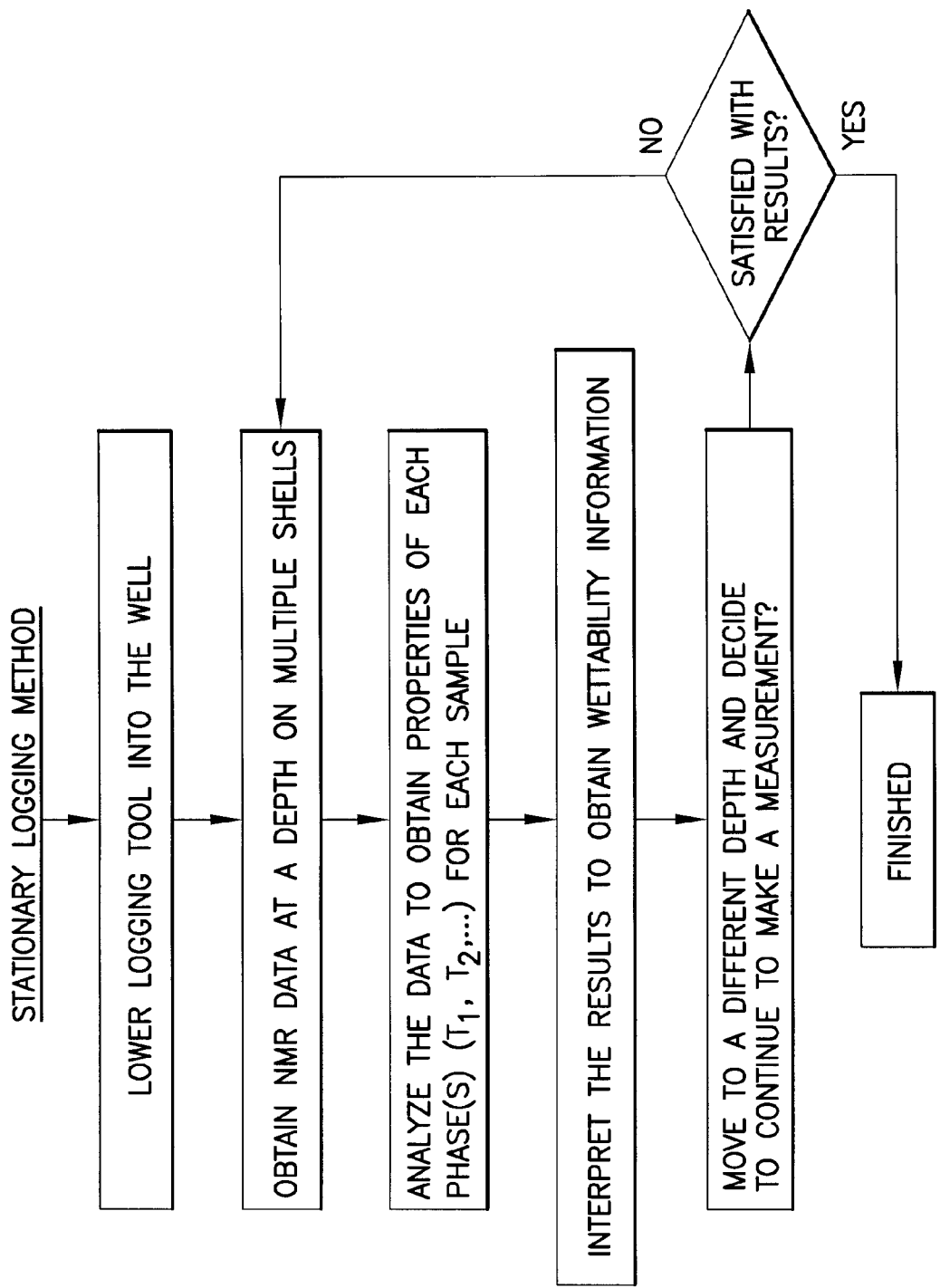
FIG. 4 illustrates at least one stationary logging method according to embodiments of the invention.

FIG. 4 shows a flowchart of at least one stationary logging method according to embodiments of the invention. First lower an NMR logging tool into the well to a specified depth. Execute the NMR pulse sequences to measure NMR response of the pore fluids at multiple DOIs for that well depth. Analyze the data obtained from the different DOIs to obtain the wettability property of the formation at this depth. The data and the interpretation of wettability may be transmit to surface. If required, move the tool to a different depth and perform the NMR measurements at this different depth to obtain the wettability property of the formation at this different depth.

Figure 5:
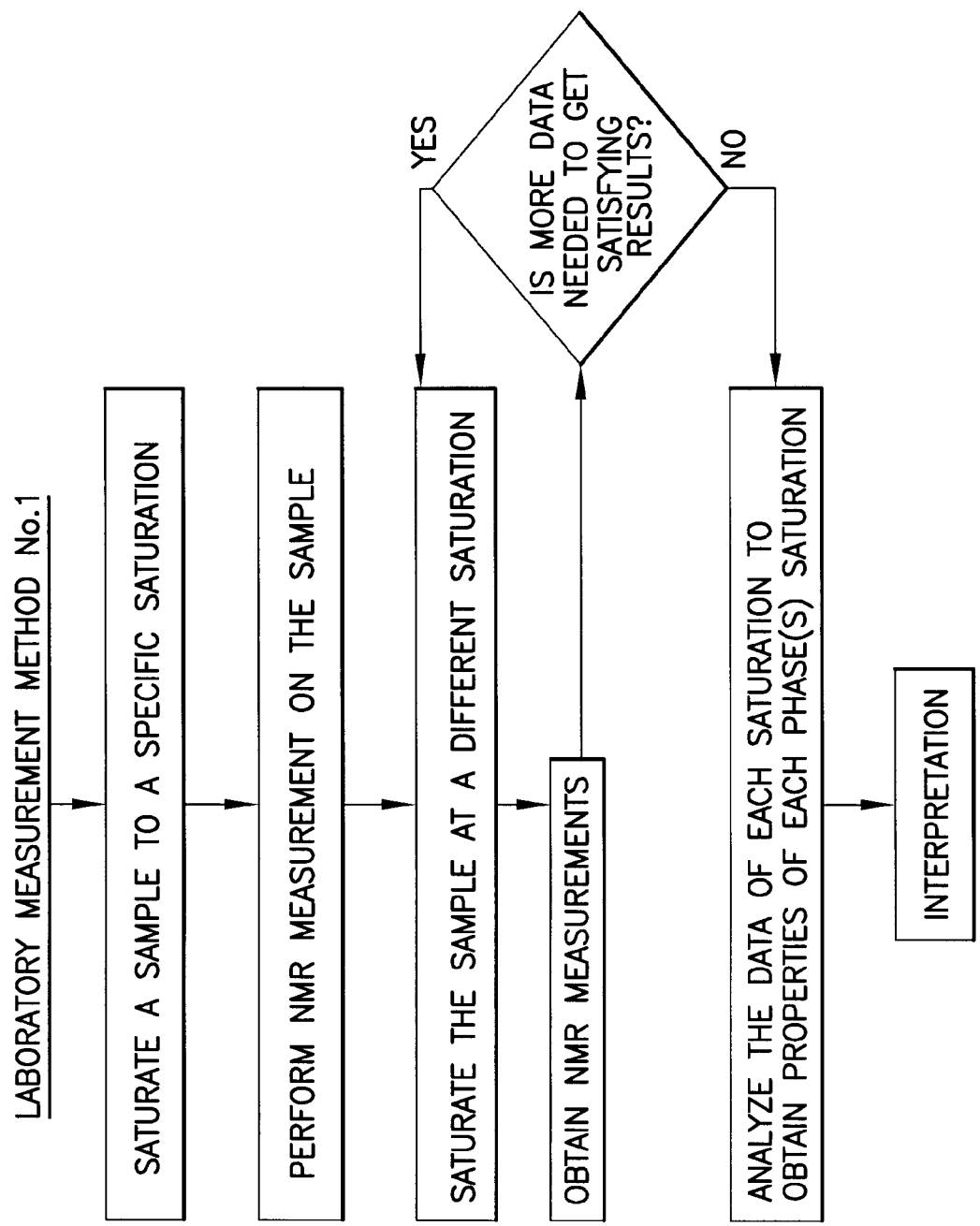
FIG. 5 illustrates at least one other laboratory measurement method (1) according to embodiments of the invention.

FIG. 5 shows a flowchart of at least one lab measurement method 1 according to embodiments of the invention. First saturate one sample to a specific partial saturation. Execute the appropriate NMR pulse sequence to measure the NMR response of the pore fluids. Saturate the sample at a second different partial saturation and perform the NMR measurement. Perform more saturations and measurement if needed. Analyze the data at all saturations to obtain the wettability property of the sample.

Figure 6:
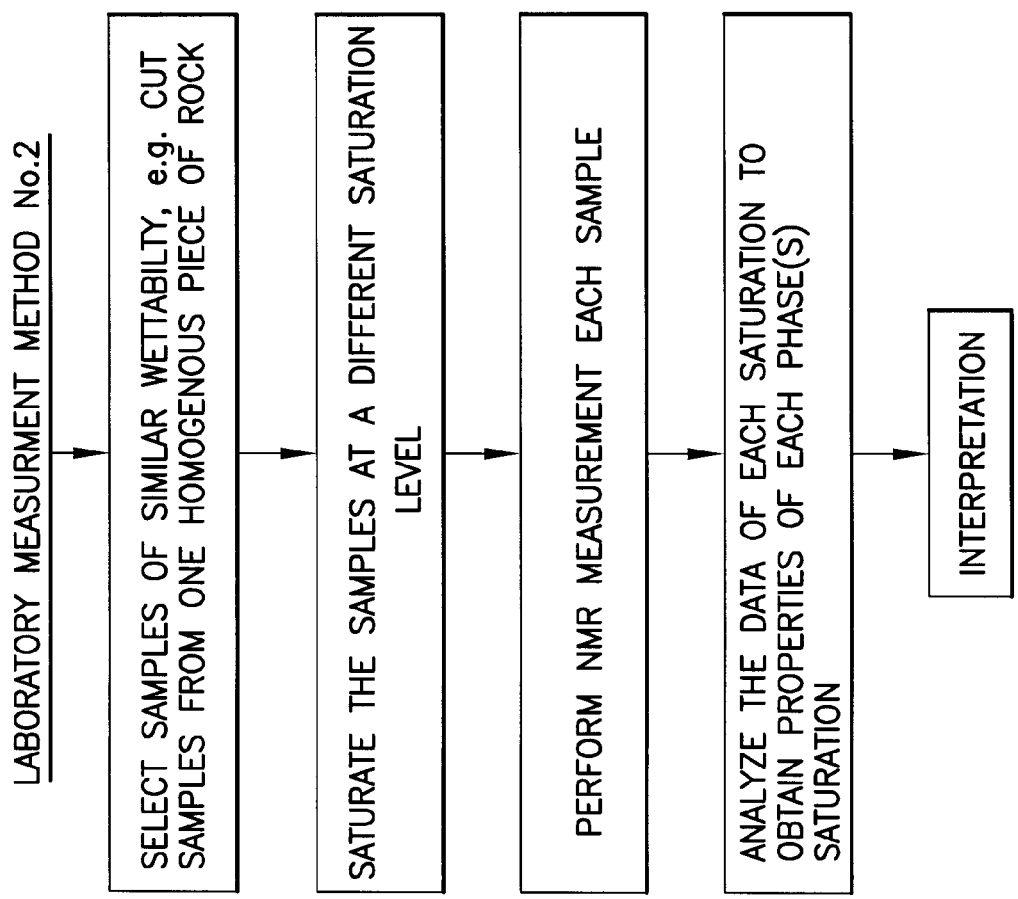
FIG. 6 illustrates at least one other laboratory measurement method (2) according to embodiments of the invention.

FIG. 6 shows a flowchart of at least one lab measurement method 2 according to embodiments of the invention. Select several samples of similar wettability properties. Saturate the samples at different partial saturation levels. Execute the appropriate NMR pulse sequences on each and all samples to obtain the NMR responses for each sample. Analyze the data at different saturations to obtain the wettability property of the rock sample.

One or more embodiments of the present invention have been described. Nevertheless, it will be understood that various modifications may be made without departing from the spirit and scope of the invention. It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for determining reservoir wettability, the method comprising:
    using a nuclear magnetic resonance (NMR) borehole logging tool to obtain at least two in situ NMR measurements, the at least two in situ NMR measurements including:
        a first in situ relaxation measurement of a first location within a reservoir formation, and
        a second in situ relaxation measurement of a second location within the reservoir formation, wherein the at least two relaxation measurements are within an approximate common characteristic region in the reservoir formation;
    determining a first saturation of a first fluid and a second fluid within the first location based upon the first in situ relaxation measurement;
    determining a second saturation of the first fluid and the second fluid within the second location based upon the second in situ relaxation measurement, wherein the first saturation is different from the second saturation; and
    comparing the first relaxation measurement at the first saturation to the second relaxation measurement at the second saturation to determine at least one wettability property in the reservoir formation.

2. The method of claim 1, wherein the approximate common characteristic region in the reservoir includes a common mineralogy.

3. The method of claim 1, wherein the comparing process includes displaying the first relaxation measurement at the first saturation and the second relaxation measurement at the second saturation on an at least two-axis graph.

4. The method of claim 3, wherein the at least two-axis graph includes a saturation axis and one of a $1/T_2$ axis, $T_{2,LM}$ axis, $T_2$ axis, average $T_2$ axis, average $1/T_2$ axis.

5. The method of claim 3, wherein the at least two-axis graph includes a saturation axis and one of a $1/T_1$ axis, $T_{1,LM}$ axis, $T_1$ axis, average $T_1$ axis, average $1/T_1$ axis.

6. The method of claim 1, wherein each of the first and second relaxation measurements includes one of $T_1$, $T_2$, or some combination thereof.

7. The method of claim 1, wherein the at least two in situ NMR measurements include a diffusion measurement of the first location and a second diffusion measurement of the second location.

8. The method of claim 7, wherein each of the first diffusion measurement and the second diffusion measurement are obtained using a diffusion-editing sequence.

9. The method of claim 7, wherein the first saturation is determined based upon the first relaxation measurement and the first diffusion measurement and the second saturation is determined based upon the second relaxation measurement and the second diffusion measurement.

10. The method of claim 1, wherein the comparing process includes generating an oil-water wettability graph.

11. The method of claim 1, wherein the at least two measurements are obtained with one of a wireline tool or a measurement-while-drilling tool.

12. The method of claim 1, wherein the at least two measurements are obtained with a nuclear magnetic resonance module in a sidewall coring tool at a selected axial depth.

13. The method of claim 1, wherein in situ NMR measurements are obtained for more than two locations, saturations are determined for more than two locations, and the in situ NMR measurements and the saturations are used to determine the at least one wettability property.

14. The method of claim 1, wherein the first fluid is water and the second fluid is at least one of an oil or a hydrocarbon.

15. A method for determining reservoir wettability, the method comprising:
    using a nuclear magnetic resonance (NMR) device to obtain at least two NMR measurements, the at least two NMR measurements including:
        a first relaxation measurement and a first diffusion measurement of a first sample from a reservoir formation, and
        a second relaxation measurement and a second diffusion measurement of a second sample from the reservoir formation, wherein the at least two samples are within an approximate common characteristic region in the reservoir formation;
    determining a first saturation of a first fluid and a second fluid within the first sample based upon the first relaxation measurement and the first diffusion measurement;
    determining a second saturation of the first fluid and the second fluid within the second sample based upon the second relaxation measurement and the second diffusion measurement, wherein the first saturation is different from the second saturation;
    comparing the first relaxation measurement at the first saturation to the second relaxation measurement at the second saturation to determine at least one wettability property in the reservoir formation.

16. The method of claim 15, wherein the approximate common characteristic region in the reservoir includes a common mineralogy.

17. The method of claim 15, wherein each of the first and second relaxation measurements includes one of $T_1$, $T_2$, or some combination thereof.

18. The method of claim 15, wherein the at least two NMR measurements are obtained with one of a wireline tool or a measurement-while-drilling tool.

19. The method of claim 15, wherein the at least two NMR measurements are obtained in a surface environment after removing at least one sample from the reservoir formation such that the at least one sample is transferred to the surface environment.

20. The method of claim 15, wherein the comparing process includes generating an oil-water wettability graph.

21. The method of claim 15, wherein each of the first diffusion measurement and second diffusion measurement are obtained using a diffusion-editing sequence.

22. The of claim 15, wherein NMR measurements are obtained from more than two samples, saturations are determined for the more than two samples, and the NMR measurements and the saturations are used to determine the at least one wettability property.

23. The method of claim 15, wherein the first fluid is water and the second fluid is at least one of an oil or a hydrocarbon.

* * * * *